US00PP14512P29

(12) United States Plant Patent
Hanes

(10) Patent No.: US PP14,512 P2
(45) Date of Patent: Feb. 3, 2004

(54) VERBENA PLANT NAMED 'RAP PINK TWO'

(50) Latin Name: *Verbena hybrida*
Varietal Denomination: Rap Pink Two

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/389,057

(22) Filed: Mar. 13, 2003

(51) Int. Cl.[7] ..... A01H 5/00

(52) U.S. Cl. ..... Plt./308
(58) Field of Search ..... Plt./308

(56) References Cited

U.S. PATENT DOCUMENTS

PP11,192 P * 1/2000 Stemkens ..... Plt./308

* cited by examiner

*Primary Examiner*—Bruce R. Campell
*Assistant Examiner*—Susan B. McCormick
(74) *Attorney, Agent, or Firm*—Jondle & Associates, PC

(57) ABSTRACT

A verbena cultivar particularly distinguished by pink colored flowers, vigorous growth and low trailing habit.

1 Drawing Sheet

Genus and species: Verbena hybrida.
Variety denomination: 'Rap Pink Two'.

BACKGROUND OF THE NEW PLANT

The present invention comprises a new and distinct cultivar of verbena, botanically known as Verbena hybrida, and hereinafter referred to by the cultivar name 'Rap Pink Two'. The new cultivar is asexually reproduced from vegetative cuttings and tissue culture resulting from the cross of the seed/pod parent 1206-3, a rose proprietary line that is unnamed and unpatented ×1194-2, a pink proprietary line that is unnamed and unpatented.

'Rap Pink Two' is a product of a planned breeding program intended to create new verbena cultivars with pink colored flowers, dark green foliage, vigorous growth and low trailing habit.

The new cultivar was created in 2001 in Gilroy, Calif. and has been asexually reproduced repeatedly by vegetative cuttings and tissue culture in Gilroy, Calif., Andijk, The Netherlands and Guatemala over a two year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF PHOTOGRAPH

This new verbena plant is illustrated by the accompanying photograph which shows blooms, buds, and foliage of the plant in full color, the colors shown being as true as can be reasonably obtained by conventional photographic procedures.

The photograph shows the mature inflorescence.

DESCRIPTION OF THE NEW CULTIVAR

The following detailed descriptions set forth the distinctive characteristics of 'Rap Pink Two'. The data, which defines these characteristics, were collected from asexual reproductions carried out in Gilroy, Calif. The plant history was taken on 9 month old plants grown in one-gallon pots, in a double poly-greenhouse under natural light and color readings were taken in the greenhouse under natural lights. Plants had been cut back numerous times prior to data readings being taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—Verbena hybrida.
*Commercial.*—Verbena.
Form: Low trailing, decumbent.
Growth and branching habit: Good vigorous habit, well-branched, full plant.
Height: From soil level to top of blooms: Approximately 10–20 cm.
Width: Approximately 60–70 cm.
Time to produce a finished flowering plant: 11 weeks.
Outdoor plant performance: Full sun; Used as a hanging plant, in mixed container planting, mass planting in a bed; some frost tolerance.
Time to initiate and develop roots: Approximately 4–10 days in the greenhouse.
Root description: Fibrous, white.

THE LEAVES

Length: 3.5–5.0 cm.
Width: 2.5–3.5 cm.
Leaf blade shape: Ovate.
Leaf margin: Pinnatisect/incised.
Apex aspect: Acute.
Base aspect: Acuminate.
Leaf color: Upper surface — RHS 137A (green); Underside — RHS 138A (green).
Texture: Hirsute.
Venation: Palmate.
Venation color: RHS 144B (green).

Petiole length: 0.5–0.7 cm.
Petiole color: RHS 144B (green).
Petiole width: 0.1–0.15 cm.
Petiole texture: Hirsute.

THE STEM

Length: 50–55 cm.
Diameter: 0.2 cm.
Internodes length: 2.0–3.5 cm.
Color: RHS 138A (green).
Texture: Hirsute.
Stem anthocyanin: No.

THE BUD

Shape: Linear.
Diameter: 0.15 cm.
Length: 1.0–1.2 cm.
Color at tight bud: RHS 62A (red-purple).

THE FLOWER

Blooming habit: Continuous throughout the growing season.
Inflorescence type: Spike.
Spike diameter: Approximately 4.5–5.0 cm.
Spike depth: Approximately 2.0–3.0 cm.
Peduncle length: 4.0–5.0 cm.
Peduncle diameter: 1.5 cm.
Peduncle color: RHS 138A (green).
Peduncle texture: Hirsute with glandular hairs of a violet hue.
Flower color: Upper petal surface is little lighter than RHS N66C (red-purple); RHS 145D (yellow-green) small 'eye spot'; Lower petal surface is RHS 65A (red-purple).
Floret form: Salverform; sessile on spikes.
Floret (limb) diameter: Approximately 1.6–1.8 cm.
Corolla tube length: Approximately 1.7–1.8 cm.
Number florets per spike: 39–48.
Petal size: Length of one lobe — 0.7–0.8 cm; width of one lobe — 0.6–0.7 cm.
Petal lobe shape: Obcordate.
Petal apex shape: Emarginated.
Petal base shape: Fused.
Petal margin: Entire.
Petal texture: Papillose.
Sepals: Five sepals whose margins are fused to each other along their length with a transparent membrane of less than 1 mm in width with one smaller sepal (7 mm) attached to the base of the calyx.
Calyx length: Approximately 0.9–1.0 cm.
Calyx width: Approximately 0.15–0.2 cm.
Calyx shape: Oblong.
Calyx apex: Acute.
Calyx color: RHS 138A (green).
Calyx texture: Glandular hairs of a violet hue.
Lastingness of individual blooms: 5–7 days.
Fragrance: None.

THE REPRODUCTIVE ORGANS

Stamens: Anthers and filaments fused to upper half of corolla tube; four anthers with two pollen sacs per anther.
Pollen amount and color: Moderate, RHS 11D (yellow).
Pistil: One style approximately 1.5 cm.
Fruit seed set: Not observed.

DISEASE AND INSECT RESISTANCE

Tolerant to mildew.

COMPARISON WITH KNOWN CULTIVARS

Differs from its female parent 00-1206-3 in the following ways: The female parent is later to flower, grows as a denser plant and is hot rose vs. pink.

Differs from its male parent 00-1194-2 in the following ways: The male parent is a smaller plant that is more upright in growth and is later to flower.

I claim:

1. A new and distinct cultivar of verbena plant as shown and described herein.

* * * * *

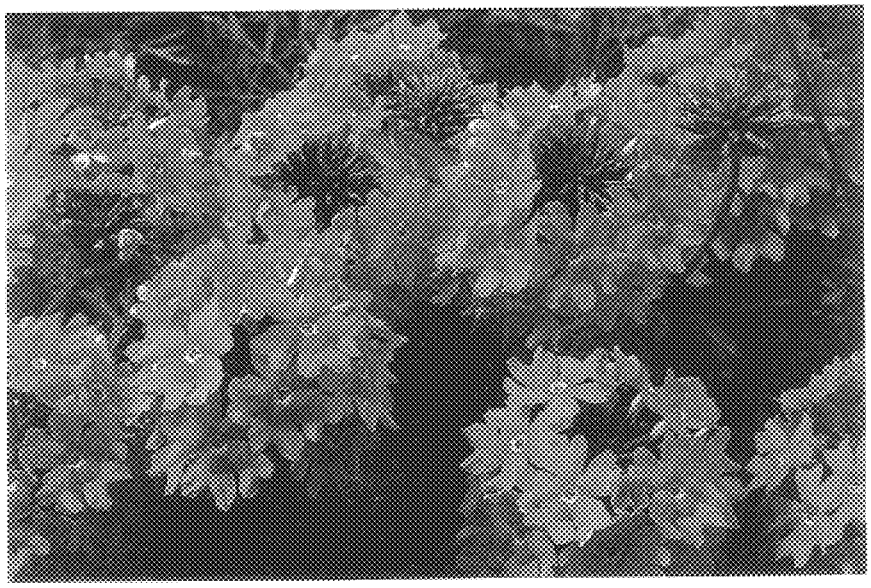

UNITED STATES PATENT AND TRADEMARK OFFICE

CERTIFICATE OF CORRECTION

PATENT NO. : PP 14,512 P2
DATED : February 3, 2004
INVENTOR(S) : Mitchell Eugene Hanes It is certified that error appears in the above-identified patent and that said Letters Patent is hereby corrected as shown below:

Column 1,
Line 1, should read -- Genus and species: Verbena hybrida x tenuisecta --
Line 7, should read -- Verbena hybrida x tenuisecta --

Column 2,
Line 13, should read -- Botanical. -- Verbena hybrida x tenuisecta --

Signed and Sealed this

Eighteenth Day of January, 2005

JON W. DUDAS
*Director of the United States Patent and Trademark Office*